United States Patent
Joshi et al.

(10) Patent No.: US 12,350,077 B2
(45) Date of Patent: Jul. 8, 2025

(54) AUTOMATED SYSTEMS AND METHODS OF OBTAINING DIAGNOSTIC IMAGES OF A PATIENT

(71) Applicants: Akash Chander Joshi, Wichita, KS (US); Aditya Joshi, Wichita, KS (US); Aditi Joshi, Wichita, KS (US)

(72) Inventors: Akash Chander Joshi, Wichita, KS (US); Aditya Joshi, Wichita, KS (US); Aditi Joshi, Wichita, KS (US)

( * ) Notice: Subject to any disclaimer, the term of this patent is extended or adjusted under 35 U.S.C. 154(b) by 111 days.

(21) Appl. No.: 18/172,124

(22) Filed: Feb. 21, 2023

(65) Prior Publication Data

US 2024/0090857 A1 Mar. 21, 2024

Related U.S. Application Data

(60) Provisional application No. 63/408,082, filed on Sep. 19, 2022.

(51) Int. Cl.
  *A61B 6/04* (2006.01)
  *A61B 6/00* (2024.01)
  *A61B 6/42* (2024.01)

(52) U.S. Cl.
  CPC .......... *A61B 6/0492* (2013.01); *A61B 6/4275* (2013.01)

(58) Field of Classification Search
  CPC ... A61B 6/0492; A61B 6/4275; A61B 5/6888; A61B 6/548; A61B 6/4014; A61B 6/4423; A61B 6/04; A61B 5/0077; A61B 6/0407; A61B 6/544; A61B 6/02; A61B 6/032; A61B 6/4266; A61B 6/46; A61B 6/545; G16H 30/20; G16H 40/63; G16H 40/67
  See application file for complete search history.

(56) References Cited

U.S. PATENT DOCUMENTS

| | | | |
|---|---|---|---|
| 4,403,337 A * | 9/1983 | Kleinman | A61B 6/589 378/96 |
| 8,249,218 B2 | 8/2012 | Bowers et al. | |
| 8,526,573 B2 | 9/2013 | Ferro, Jr. | |
| 2012/0039439 A1* | 2/2012 | Kia | A61B 6/5205 378/62 |
| 2013/0046176 A1* | 2/2013 | Mistretta | A61B 6/481 600/431 |
| 2013/0279783 A1* | 10/2013 | Schmitt | A61B 6/032 382/131 |
| 2014/0003577 A1* | 1/2014 | Ferro | G06Q 20/10 378/62 |

(Continued)

FOREIGN PATENT DOCUMENTS

WO 2020168195 A1 8/2020

*Primary Examiner* — Alexei Bykhovski
(74) *Attorney, Agent, or Firm* — Hovey Williams LLP; Kameron D. Kelly

(57) ABSTRACT

An automated method and kiosk for obtaining diagnostic images of a patient are provided. The method is performed by receiving personal information about the patient at the automated kiosk, obtaining, with a diagnostic imaging system at the automated kiosk, a first diagnostic image of the patient from a first projection angle relative to at least one body part of the patient, and obtaining, with the diagnostic imaging system, a second diagnostic image of the patient from a second projection angle relative to the at least one body part. The method steps are performed without real-time control of the automated kiosk by another human.

13 Claims, 5 Drawing Sheets

(56) References Cited

U.S. PATENT DOCUMENTS

| | | |
|---|---|---|
| 2015/0248536 A1 | 9/2015 | Tawil et al. |
| 2016/0085935 A1 | 3/2016 | Waterson et al. |
| 2018/0070908 A1* | 3/2018 | Netabayashi ........ A61B 6/4035 |
| 2019/0076105 A1* | 3/2019 | Haase .................... A61B 6/507 |
| 2022/0031273 A1* | 2/2022 | Lewis .................... A61B 6/527 |
| 2022/0180339 A1* | 6/2022 | Shell ......................... A61L 2/10 |

* cited by examiner

AUTOMATED SYSTEMS AND METHODS OF OBTAINING DIAGNOSTIC IMAGES OF A PATIENT

CROSS-REFERENCE TO RELATED APPLICATIONS

This application claims priority to Application No. 63/408,082, filed on Sep. 19, 2022, and entitled AUTOMATED ACQUISITION OF MEDICAL IMAGING, which is hereby incorporated by reference in its entirety.

BACKGROUND

There are many barriers to quickly and conveniently obtaining radiological scans within the present day medical infrastructure. For example, the availability of medical resources and professionals may be limited to some segments of the population, such as those that live in rural or isolated areas. On the other hand, the limited availability of medical resources and professionals in populated areas sometimes results in backlogs and delays in obtaining radiological scans and/or obtaining the results from such radiological scans. In either scenario, these barriers create a burden to those in need of medical care and can even lengthen a patient's time to recovery. Even when medical resources such as radiology equipment are readily available, the equipment is typically operated by trained medical professionals. Thus, the ability of a medical facility to provide radiological services is dependent on the availability of trained medical professionals to perform the scans. In addition, radiological equipment is expensive and generally only available at large medical facilities, such as hospitals or clinics.

Thus, it is desirable to provide radiological services that are not dependent on medical equipment operated by human personnel.

BRIEF SUMMARY

Provided herein is a diagnostic imaging kiosk. The kiosk comprises an enclosure having an interior sized to receive a patient, a diagnostic imaging system, a body positioning system, and a controller. The controller is configured to (a) receive personal information about the patient, (b) determine, based on the personal information, exposure factor settings for imaging at least one body part of the patient with the diagnostic imaging system, (c) verify, with the body positioning system, that the body part of the patient is positioned for imaging by the diagnostic imaging system, and (d) obtain, using the determined exposure factor settings, at least one diagnostic image of the body part.

In one embodiment, the controller is configured to determine, based on the personal information, an imaging procedure for imaging at least one body part of the patient with the diagnostic imaging system. The imaging procedure comprises taking a plurality of diagnostic images from different projection angles relative to the at least one body part. The controller is also configured to verify, with the body positioning system, that the at least one body part of the patient is positioned for imaging by the diagnostic imaging system, and obtain, using the imaging procedure, the plurality of diagnostic images of the at least one body part.

Also provided herein is an automated method of obtaining diagnostic images of a human patient. The method comprises (a) receiving personal information about the patient at an automated kiosk, (b) obtaining, with a diagnostic imaging system at the automated kiosk, a first diagnostic image of the patient from a first projection angle relative to at least one body part of the patient, and (c) obtaining, with the diagnostic imaging system, a second diagnostic image of the patient from a second projection angle relative to the at least one body part, wherein steps (a) through (c) are performed without real-time control of the automated kiosk by another human.

BRIEF DESCRIPTION OF THE DRAWINGS

Various embodiments of the present disclosure are described in detail below with reference to the attached drawing figures, wherein.

DETAILED DESCRIPTION

Figure 1:
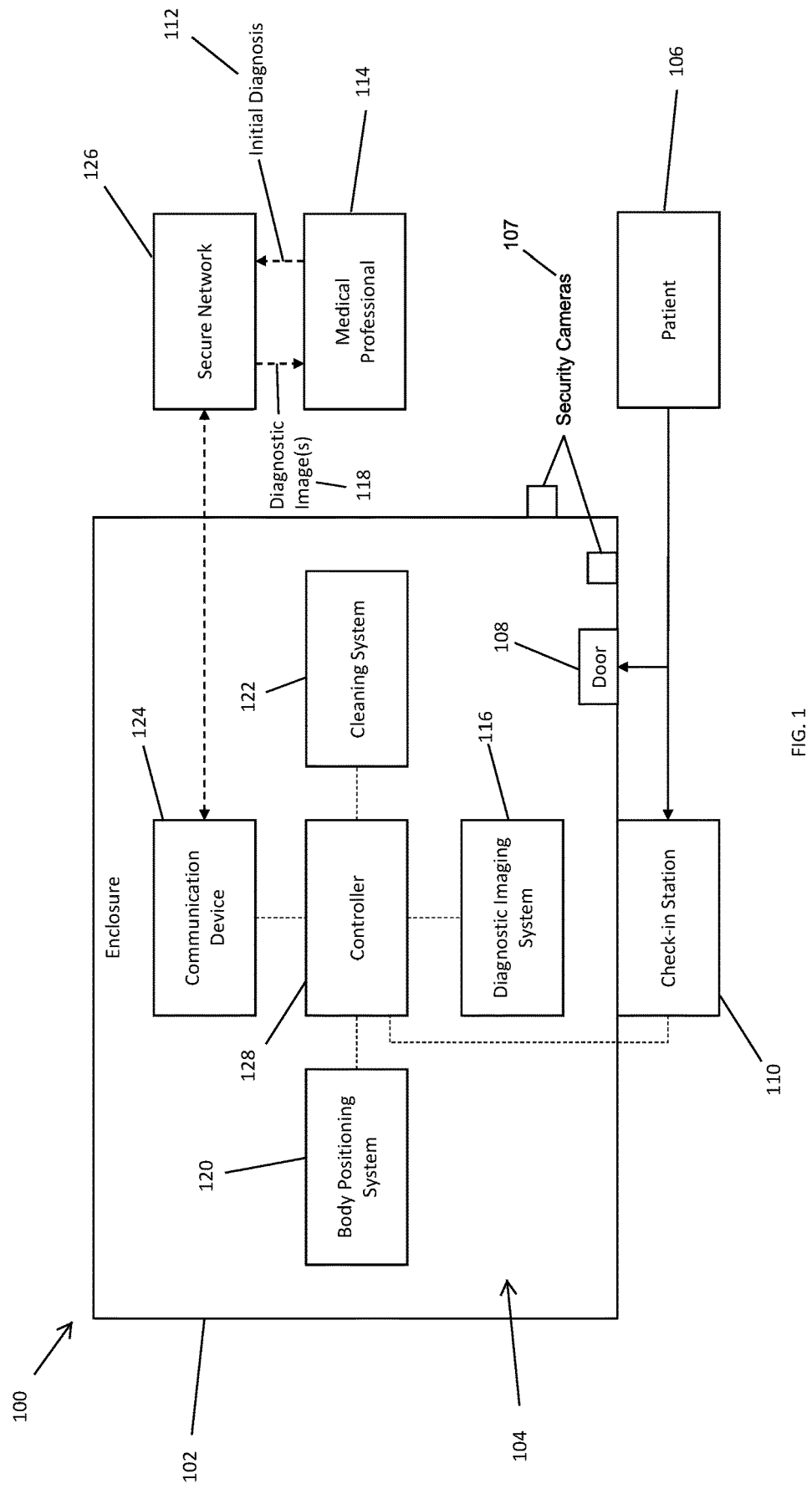
FIG. 1 is a block diagram illustrating an example diagnostic imaging kiosk.

The present disclosure is directed to an automated diagnostic imaging kiosk for performing radiological imaging (e.g., X-ray, computerized tomography (CT), bone density, mammography, or magnetic resonance scanning). The systems and methods described herein automate the basic functionality of radiological imaging equipment to enable radiological images to be obtained without human intervention or real-time control of the kiosk by a medical professional. Accordingly, the systems and methods described herein increase the access of radiological imaging equipment to patients in need of accurate medical diagnoses. For example, rather than being limited to hospitals and clinics, the automated kiosk may be delivered and used in places where there is a demand for scans and limited access to these traditional medical facilities. In addition to increasing access to this equipment, the automation described herein enables the kiosk to be accessible to patients 24/7 without the need for a medical professional to be present to operate the equipment.

Although radiological scanning devices exist in the present day medical infrastructure, none exist in a form that is both automated and accessible in a non-clinical setting. The current process of getting a scan requires a patient to visit a hospital or clinic and wait for medical professionals to conduct the scan. For example, current radiological scanners require medical professionals to perform actions like moving a bed, adjusting a patient's body position relative to a scanner, and/or adjusting the position of a detector plate relative to the patient. In addition, due to their bulky nature, these scanners are only present in clinical settings, which are limited in quantity and accessibility.

In one embodiment of the present disclosure, the diagnostic imaging kiosk includes automated diagnostic imaging equipment, a computing device for controlling the diagnostic imaging equipment, and software for administering service requests and controlling radiological exam operations. The kiosk automates basic functionalities of radiological imaging, such as adjusting a bed based on the specific scan being performed, directing a patient to position themselves in a certain way relative to the imaging equipment, adjusting the position of the diagnostic imaging equipment to obtain images from one or more projection angles, and determining exposure factor settings. In addition, unique patient accounts may be generated to provide supplemental information to a patient that may not be available in traditional clinical settings. For example, the amount of radiation that the patient is subjected to, the number of scans the patient has completed over a selected amount of time, and the progression of a patient's medical issues over time may all be associated with a unique patient account that is accessible to the patient, such as at an online portal.

By decoupling the providing of radiological services from the need for human intervention in providing these services, radiological scans may be performed on those with limited access to diagnostic imaging equipment and the trained professionals required to operate this equipment. As such, the systems and methods described herein provide a modular and/or easily deployable diagnostic imaging kiosk for use in remote locations and/or for use in supplementing radiological services in higher density population centers.

The present invention may be understood more readily by reference to the following detailed description and the examples provided therein. It is to be understood that this disclosure is not limited to the specific methods, formulations, and conditions described, as such may vary. It is also to be understood that the terminology used herein is for the purpose of describing particular aspects of the disclosed embodiments only and is not intended to be limiting.

As used herein, the terms "a," "an," and "the" mean one or more.

As used herein, the term "and/or," when used in a list of two or more items, means that any one of the listed items can be employed by itself or any combination of two or more of the listed items can be employed. For example, if a system is described as containing components A, B, and/or C, the system can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

Referring now to FIG. 1, a diagnostic imaging kiosk 100 is provided that includes an enclosure 102. Enclosure 102 includes an interior 104 sized to receive a patient 106, and a door 108 that enables patient 106 to enter and exit enclosure 102. One or more security cameras 107 can be place outside and/or inside the enclosure 102 to promote safety for the patient 106 and security for the kiosk 100. As described above, one or more types of radiological imaging are performed within enclosure 102. Accordingly, enclosure 102 is designed to prevent radiation from escaping enclosure 102 and inadvertently impacting people or objects exterior of enclosure 102. Enclosure 102 may be at least partially lined with radiation absorbing and/or repelling material, such as lead, to prevent the radiation from escaping enclosure 102. In addition, kiosk 100 may only be operable to perform radiological scans when it is determined door 108 is closed and sealed, as will be described in more detail below.

A check-in station 110 is provided outside of enclosure 102 to be accessible by a patient 106 in need of radiological scanning. In some embodiments, check-in station 110 receives (directly, wirelessly, and/or via the internet) an input of personal information by patient 106. Example personal information includes, but is not limited to, the patient's identity, the patient's medical information and history, the patient's body weight, the patient's height, symptoms experienced by the patient, and the at least one body part of patient 106 that is desired to be scanned. Alternatively, check-in station 110 queries patient 106 with a series of questions, and patient 106 inputs personal information in response to the questions. The questions may be targeted to gather the personal information described above and/or to determine an initial diagnosis for patient 106, such as by querying patient 106 on their symptoms. Further, check-in station 110 can include a weighing scale and/or height measuring equipment. The height and weight output of such equipment can be used to verify and/or calculate body mass index (BMI), which can then be used to determine exposure parameters. Based on this personal information, kiosk 100 generates the initial diagnosis of patient 106, and determines an imaging procedure based on the initial diagnosis, as will be described in more detail below.

In some embodiments, an initial diagnosis 112 is provided to kiosk 100 from a medical professional 114. For example, medical professional 114 may perform an examination on patient 106 to determine whether a radiological scan is needed to fully diagnose the patient's condition. In such embodiments, initial diagnosis 112 is provided to kiosk 100 and an imaging procedure is determined based on initial diagnosis 112.

A diagnostic imaging system 116 for performing the radiological scans is included within enclosure 102. Example radiological scans that may be performed by diagnostic imaging system 116 include, but are not limited to, X-ray, computerized tomography (CT), bone density, mammography, or magnetic resonance scans. Accordingly, in one embodiment, diagnostic imaging system 116 includes at least one emitter for discharging a scanning beam towards patient 106, and at least one detector for generating a diagnostic image 118 from scanning beam (See FIGS. 2-4). The emitters described below may be cold cathode type X-ray tubes. The detectors described below may be a photostimulable phosphor plates, or direct or indirect flat panel detectors. The emitters and/or detectors may have a rectangular or keyhole/arc/curved design.

Kiosk 100 will now be described in the context of performing X-ray radiological scans. However, it should be understood kiosk 100 may also be designed to perform the other radiological scans disclosed herein.

In operation, diagnostic imaging system 116 obtains a plurality of diagnostic images 118 from different projection angles relative to the body part of patient 106 to be scanned. In general, there are two main categories of X-ray scans. The first category includes anterior/posterior (AP) scans and posterior/anterior (PA) scans. AP X-rays produce an image when X-ray radiation passes from the front (anterior) to the back (posterior) of the body. PA images are produced when X-rays pass from the back to the front of the body. While both types of scans are frequently used, PA scans limit radiation exposure to a patient's eyes. The second category includes lateral scans, where X-ray radiation passes through one side of the body to the other. As will be described in more detail below, the emitter and/or detector are positionable to obtain diagnostic images 118 from these different projection angles. In addition, various oblique projection images (other true PA, AP and lateral images) could also be obtained with this system.

A body positioning system 120 for directing patient 106 to locate itself at a particular location, and at a particular orientation, within enclosure 102 is also included in kiosk 100. In one embodiment, body positioning system 120 includes an audio/video (AV) device. AV device is operable to interact with patient 106 via at least one of visual, written, or auditory feedback. The visual, written, or auditory feedback is provided to direct/instruct patient 106 on how to position itself or a body part thereof for imaging. The visual feedback may be provided via illustrations displayed on the AV device, such as illustrations showing an example patient positioning itself in the same manner as patient 106 should be positioned. The visual feedback may also be in the form of visual projections within interior 104 showing how patient 106 should position certain body parts within enclosure 102. The written feedback may be provided on AV device in the form of textual guidance, and the auditory feedback may be provided from AV device in the form of audio guidance. In one embodiment, body positioning system 120, may direct the diagnostic imaging system 116 to move and reposition emitters and/or detectors around patient 106 to obtain projection images from various angles.

In some embodiments, body positioning system 120 is also used to verify that patient 106 is accurately positioned for scanning prior to performing the scan, and/or to verify that patient 106 has followed the directions provided from the AV device. In such embodiments, body positioning system 120 includes a verification scanner (e.g., a camera) for determining the position of patient 106 within enclosure 102 in real-time. This real-time feedback enables kiosk 100 to operate automatedly without real-time control by another human.

In one embodiment or in combination with any embodiments mentioned herein, kiosk 100 includes a cleaning system 122 for disinfecting interior 104 of kiosk 100 prior to receiving a new patient therein. Cleaning system 122 may include an ultraviolet disinfecting device and/or a device that sprays a disinfecting liquid within interior 104.

In one embodiment or in combination with any embodiments mentioned herein, kiosk 100 includes a communication device 124 for providing diagnostic images 118 obtained by diagnostic imaging system 116 to a medical professional 114 that is remote from kiosk 100 for further diagnosis. Diagnostic images 118 may be provided to the same or a different medical professional that initially examines patient 106 and provides initial diagnosis 112 to kiosk 100.

In one embodiment or in combination with any embodiments mentioned herein, communication device 124 receives initial diagnosis 112 from medical professional, and a controller 128 determines an imaging procedure therefrom, as described below. Initial diagnosis 112 and diagnostic images 118 are transferred between kiosk 100 and medical professional 114 via a secure network 126. For example, initial diagnosis 112, including personal information about patient 106, and diagnostic images 118 may be stored in a vendor neutral archive or a picture archiving and communication system (PACS) prior to being transmitted between kiosk 100 and medical professional 114. Accordingly, medical professional 114 is able to diagnose patient 106 and refer patient 106 to kiosk 100 for the performance of radiological scans, to analyze diagnostic images 118 obtained by kiosk 100, and to then provide a full diagnosis to patient 106 based on the analysis.

As described above, kiosk 100 is configured to obtain diagnostic images 118 without human intervention or real-time control of kiosk 100 by a medical professional. Accordingly, kiosk 100 includes controller 128 communicatively coupled with the systems and devices of kiosk 100 to provide automated control thereof.

Figure 5:
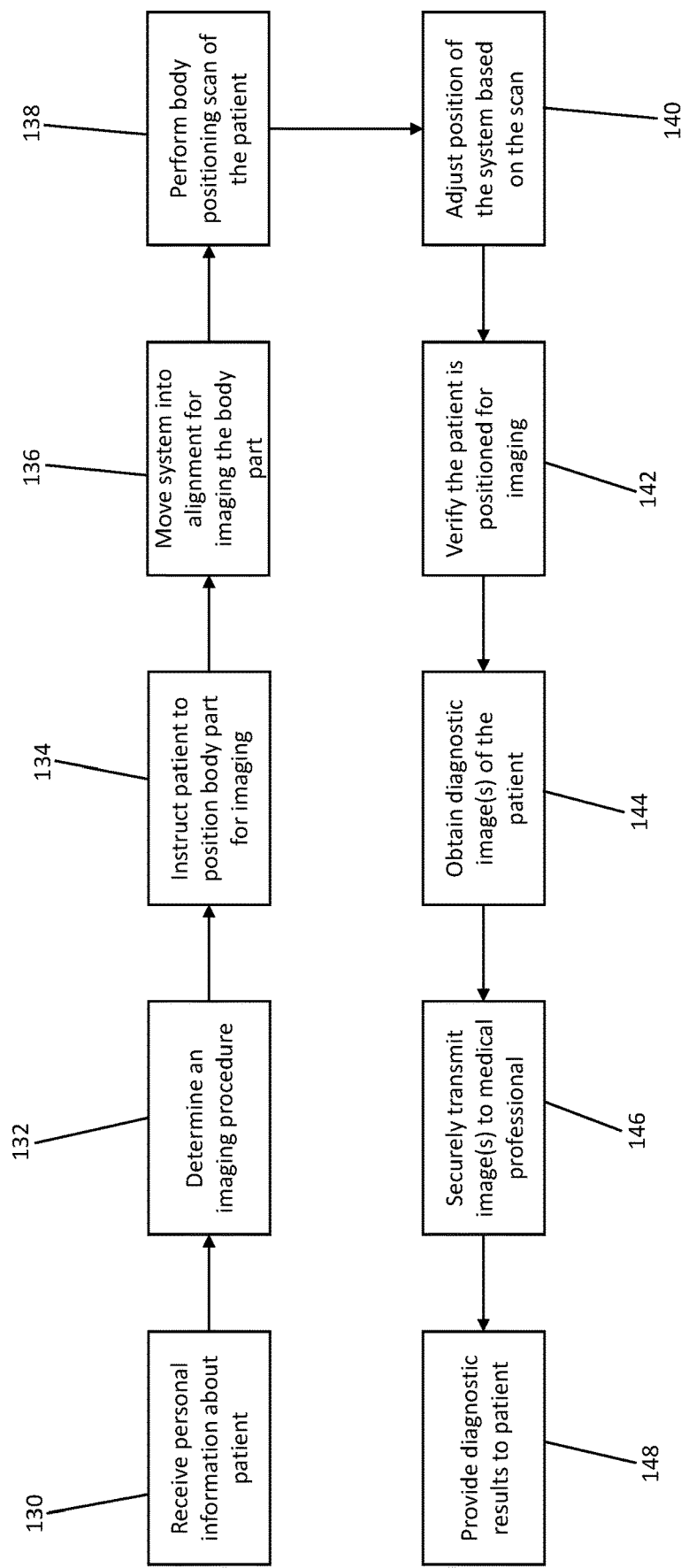
FIG. 5 is a flow diagram illustrating an example automated method of obtaining diagnostic images of a patient.

With reference to FIGS. 1 and 5, in one embodiment or in combination with any embodiments mentioned herein, kiosk 100 receives 130 personal information from patient 106 at check-in station 110 prior to performing a scan. Based on the input of this personal information, controller 128 verifies that patient 106 is eligible to be scanned and unlocks door 108 to allow patient 106 to enter enclosure 102. Also based on the input of this personal information, controller 128 determines 132 an imaging procedure for imaging at least one body part of patient 106 with diagnostic imaging system 116. The imaging procedure includes at least one of exposure factor settings (e.g., milliamperage, exposure time, and kilovoltage peak) for imaging the at least one body part, an initial imaging position of diagnostic imaging system 116 relative to the at least one body part, how many diagnostic images are to be taken, or the different projection angles from which to take the plurality of diagnostic images 118.

After patient 106 enters enclosure 102, controller 128 verifies that door 108 is closed and sealed to prevent the escape of radiation during performance of the scan, as described above. Based on the determined imaging procedure, controller 128 then instructs 134, with body positioning system 120, patient 106 to position itself for imaging by diagnostic imaging system 116. For example, patient 106 may be directed to position itself at a particular location within interior 104, and/or to orient a body part in a particular way relative to diagnostic imaging system 116.

In accordance with the imaging procedure, in one embodiment or in combination with any embodiments mentioned herein, controller 128 moves 136 diagnostic imaging system 116 to the initial imaging position. The initial imaging position may be determined based on the body part of patient 106 to be scanned. For example, if the patient's leg is the body part to be scanned, controller 128 moves 136 diagnostic imaging system 116 to an initial height that enables the patient's leg to be scanned.

Controller 128 then performs 138, with body positioning system 120, a body positioning scan of patient 106 to verify that the at least one body part of patient 106 is positioned for imaging by diagnostic imaging system 116. For example, body positioning system 120 may scan patient 106 to determine its body profile and positioning relative to diagnostic imaging system 116. This body positioning scan enables kiosk 100 to determine the body profile and positioning of patient 106 in real-time. Accordingly, controller 128 selectively adjusts 140 the position of diagnostic imaging system 116 from the initial imaging position to a final imaging position to account for any differences in the body profiles of different patients, for example.

In one embodiment or in combination with any embodiments mentioned herein, controller 128 verifies 142 patient 106 is positioned for imaging with the body positioning scan. Once verified, body positioning system 120 provides directions for the patient to remain stationary while diagnostic imaging system 116 performs the imaging procedure. For example, controller 128 obtains 144 diagnostic images 118 of patient 106 from one or more projection angles, and then securely transmits 146 diagnostic images 118 over secure network 126 to enable further diagnosis to be performed, such as by medical professional 114 that is remote from kiosk 100. Medical professional 114 may then provide 148 results of the further diagnosis to patient 106. The results may be provided at kiosk 100 or at a secure online portal, for example.

Figure 2:
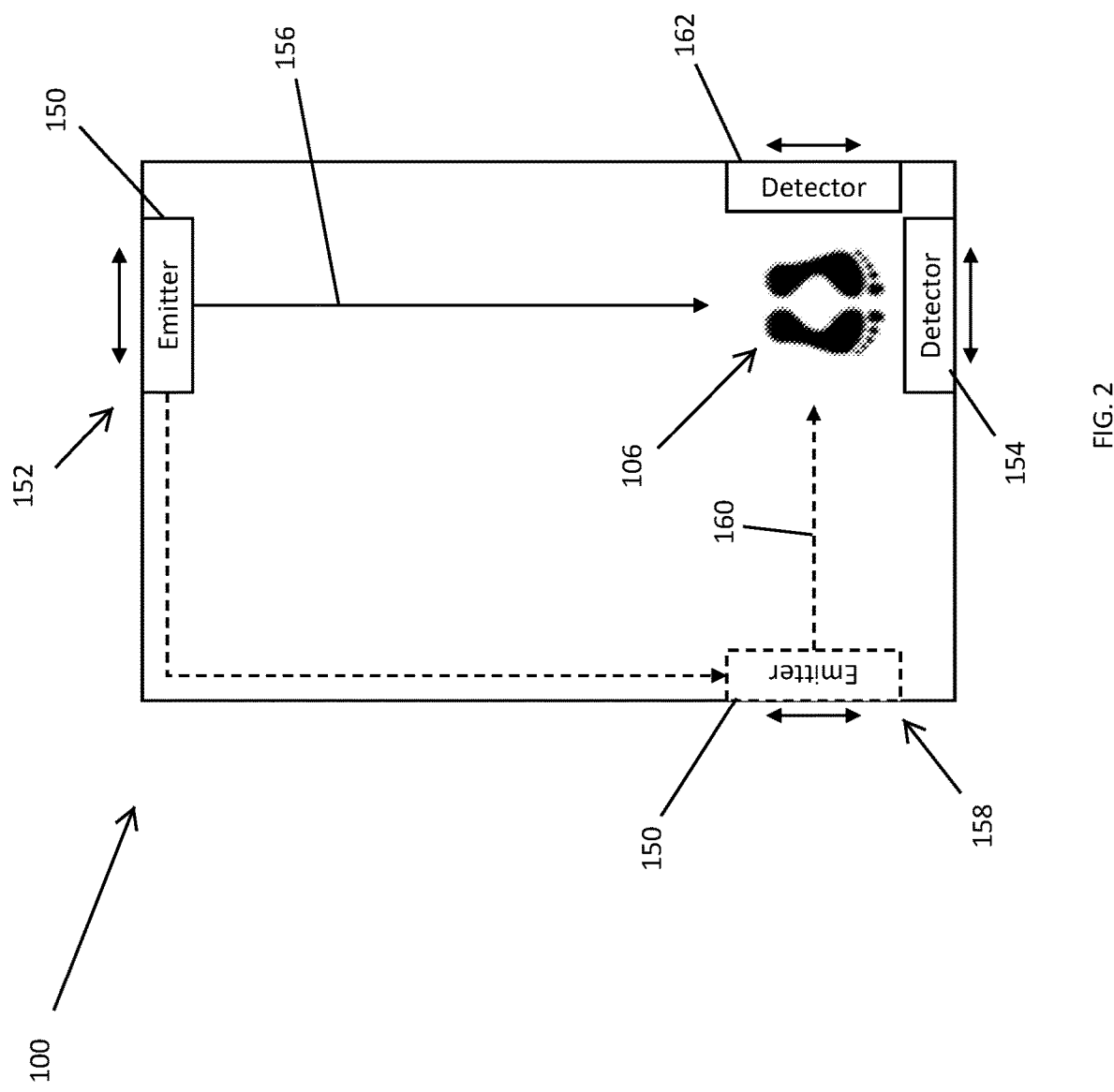
FIG. 2 is an interior view of one embodiment of the kiosk shown in FIG. 1.

Referring to FIG. 2, diagnostic imaging system 116 (shown in FIG. 1) includes a single emitter 150 that is movable to obtain diagnostic images 118 (shown in FIG. 1) from different projection angles relative to patient 106. For example, emitter 150 is initially positioned at a first projection angle 152 relative to patient 106, and a first detector 154 is positioned opposite emitter 150 to enable diagnostic images 118 to be obtained. Once located at the final imaging position as described above, emitter 150 projects a first scanning beam 156 towards patient 106 to obtain a first diagnostic image from first projection angle 152. Based on the determined imaging procedure, additional diagnostic images may be obtained to fully diagnose the patient's condition. Accordingly, emitter 150 is movable from first projection angle 152 to a second projection angle 158 that is different from first projection angle 152. That is, first and second projection angles 152 and 158 are selected to obtain different views of the patient's body part.

In one embodiment or in combination with any embodiments mentioned herein, additional directions may be provided to patient 106 from body positioning system 120 (shown in FIG. 1) prior to performing imaging from second projection angle 158. Adjustments to the positioning of emitter 150 and additional body positioning verification may also be performed. Emitter 150 may then project a second scanning beam 160 towards patient 106 to obtain a second diagnostic image from second projection angle 158. The second diagnostic image is obtained by a second detector 162 positioned opposite emitter 150.

Figure 3:
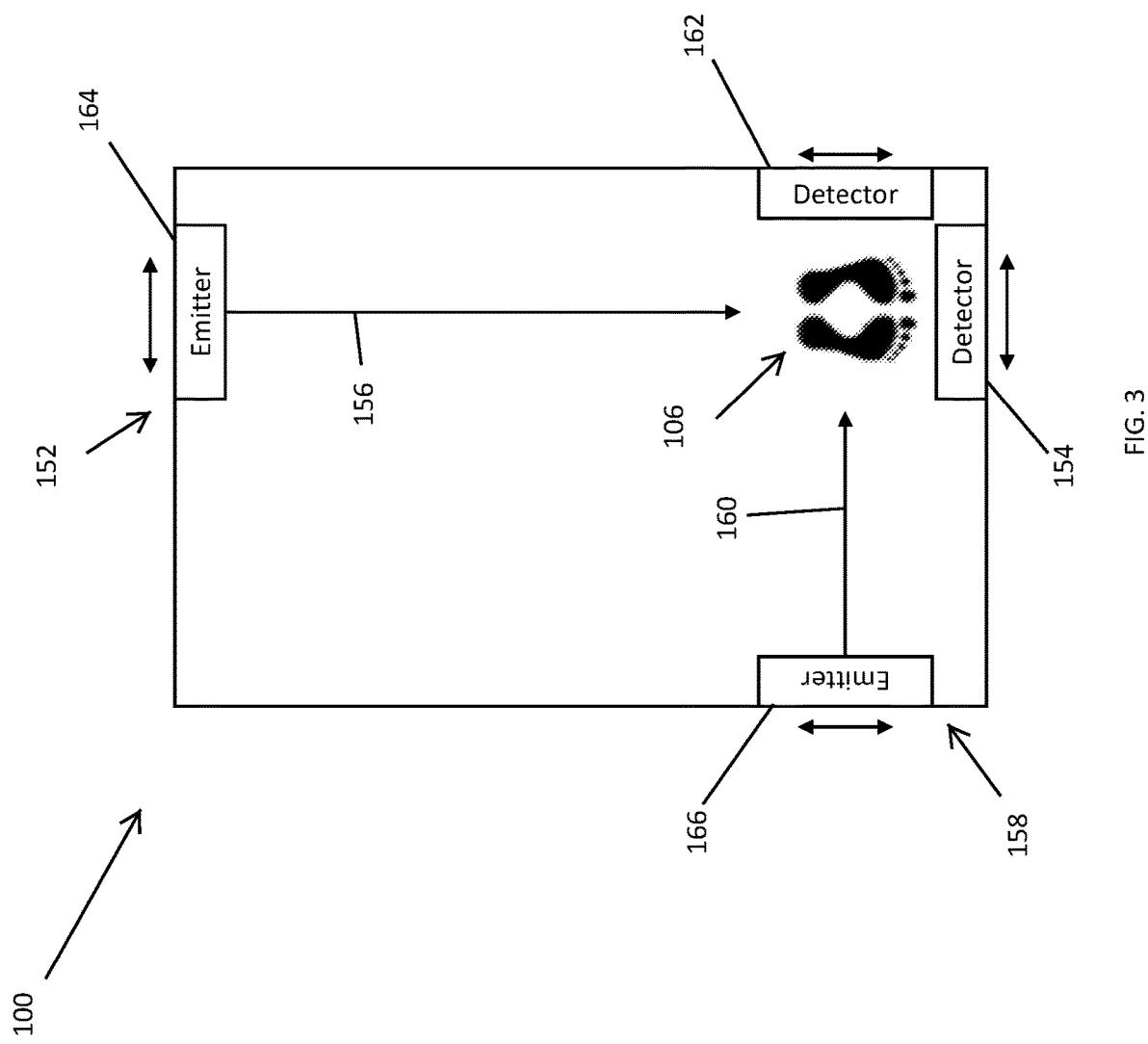
FIG. 3 is an interior view of another embodiment of the kiosk shown in FIG. 1.

Referring to FIG. 3, diagnostic imaging system 116 (shown in FIG. 1) includes a first emitter 164 and a second emitter 166 for obtaining diagnostic images 118 (shown in FIG. 1) from different projection angles relative to patient 106. For example, first emitter 164 is positioned at first projection angle 152 relative to patient 106, and second emitter 166 is positioned at second projection angle 158 relative to patient 106. First detector 154 is positioned opposite first emitter 164, and second detector 162 is positioned opposite second emitter 166.

Once located at the respective final imaging positions as described above, first emitter 164 projects first scanning beam 156 towards patient 106 to obtain a first diagnostic image from first projection angle 152, and second emitter 166 projects second scanning beam 160 towards patient 106 to obtain a second diagnostic image from second projection angle 158. In one embodiment, first and second scanning beams 156 and 160 are projected towards patient 106 simultaneously. Accordingly, multiple diagnostic images may be obtained without requiring adjustments to the positions of the patient and/or diagnostic imaging system 116 to be made, and without requiring an additional verification step of the patient's body position relative to diagnostic imaging system 116.

Figure 4:
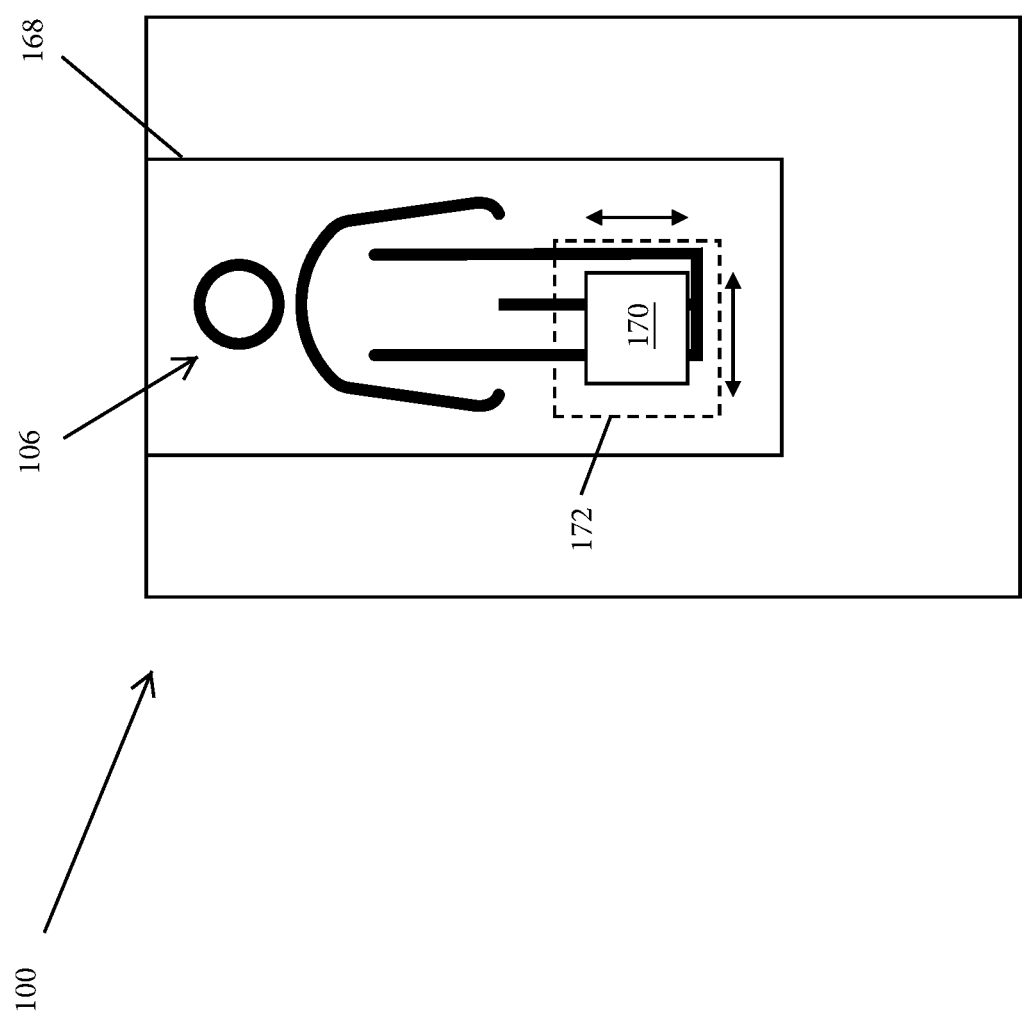
FIG. 4 is an interior view of yet another embodiment of the kiosk shown in FIG. 1.

Referring to FIG. 4, kiosk 100 further includes an examination table 168 within enclosure 102. In one embodiment or in combination with any embodiments mentioned herein, examination table 168 is oriented to enable patient 106 to lie in a supine position thereon. Examination table 168 may be included within kiosk 100 to enable scans to be performed on patients with limited mobility, or that are unable to stand on their own. Accordingly, an emitter 170 is positioned above examination table 168, and a detector 172 is positioned opposite emitter 170 below examination table 168 and/or patient 106. The positions of emitter 170 and detector 172 are adjustable for moving to a final imaging position, as described above. Alternatively, the position of examination table 168 is adjustable, such as by controller 128 (shown in FIG. 1), to orient patient 106 for imaging.

As illustrated in FIGS. 2-4, the position of the emitters and detectors is selectively adjustable for moving to the final imaging position. The emitters and detectors are illustrated as being movable laterally relative to patient 106. However, it should be understood that the position of the emitters and detectors may be adjusted in any direction (i.e., laterally or vertically) to achieve the final imaging position.

The preferred forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The invention claimed is:

1. An automated diagnostic imaging kiosk comprising:
an enclosure comprising an interior sized to receive a patient;
a diagnostic imaging system;
a body positioning system;
a cleaning system configured to disinfect the enclosure; and
a real-time controller communicatively coupled to the diagnostic imaging system, the body positioning system, and the cleaning system, wherein the real-time controller is configured to:
receive personal information about the patient;
determine, based on the personal information, an imaging procedure for imaging at least one body part of the patient with the diagnostic imaging system, wherein the imaging procedure comprises taking a plurality of diagnostic images from different projection angles relative to the at least one body part, wherein the diagnostic imaging system comprises a single emitter that is movable via the real-time controller relative to the patient to position the single emitter at the different projection angles;
verify, with the body positioning system, that the at least one body part of the patient is positioned for imaging by the diagnostic imaging system; and
obtain, using the imaging procedure, the plurality of diagnostic images of the at least one body part.

2. The diagnostic imaging kiosk in accordance with claim 1, wherein the diagnostic imaging system comprises a plurality of emitters each positioned at different projection angles relative to the at least one body part, wherein the body positioning system comprises a verification scanner configured to determine a real-time position of the patient within the enclosure.

3. The diagnostic imaging kiosk in accordance with claim 1, wherein the body positioning system provides directions for the patient to remain stationary while the diagnostic imaging system performs the imaging procedure.

4. The diagnostic imaging kiosk in accordance with claim 1, wherein the different projection angles comprise at least two of an anterior/posterior projection angle, a lateral projection angle, and various oblique angles.

5. The diagnostic imaging kiosk in accordance with claim 1, wherein the imaging procedure further comprises at least one of exposure factor settings for imaging the at least one body part, an initial imaging position of the diagnostic imaging system relative to the at least one body part, how many diagnostic images are to be taken, or the different projection angles from which to take the plurality of diagnostic images.

6. An automated method of obtaining diagnostic images of a human patient, the method comprising:
   (a) receiving personal information about the patient at an automated kiosk;
   (b) obtaining, with a diagnostic imaging system at the automated kiosk, a first diagnostic image of the patient from a first projection angle relative to at least one body part of the patient; and
   (c) obtaining, with the diagnostic imaging system, a second diagnostic image of the patient from a second projection angle relative to the at least one body part, wherein steps (a) through (c) are performed in a non-clinical setting without real-time control of the automated kiosk by another human, wherein the automatic kiosk comprises a real-time controller communicatively coupled to the diagnostic imaging system.

7. The automated method in accordance with claim 6, further comprising automatically determining, based on the personal information, exposure factor settings for imaging the at least one body part with the diagnostic imaging system.

8. The automated method in accordance with claim 6, wherein the obtaining of step (b) is performed with a first emitter oriented at the first projection angle, and the obtaining of step (c) is performed with a second emitter oriented at the second projection angle.

9. The automated method in accordance with claim 6, wherein the obtaining of steps (b) and (c) is performed with a single emitter that is movable relative to the patient to position the single emitter at the first and second projection angles.

10. The automated method in accordance with claim 6, further comprising providing the first and second diagnostic images for further diagnosis by a medical professional that is remote from the automated kiosk.

11. The automated method in accordance with claim 6, wherein, prior to the obtaining of step (b) or (c), the method further comprises:

scanning the patient to determine the position of the at least one body part relative to the diagnostic imaging system; and selectively moving, based on the scan, the diagnostic imaging system to a final imaging position relative to the at least one body part.

12. The automated method in accordance with claim 6, wherein the personal information comprises one or more of the patient's identity, the patient's medical information and history, symptoms experienced by the patient, and the at least one body part to be scanned.

13. An automated diagnostic imaging kiosk comprising:
   an enclosure comprising an interior sized to receive a patient;
   a diagnostic imaging system;
   a body positioning system;
   a cleaning system configured to disinfect the enclosure; and
   a real-time controller communicatively coupled to the diagnostic imaging system, the body positioning system, and the cleaning system, wherein the real-time controller is configured to:
   receive personal information about the patient;
   determine, based on the personal information, an imaging procedure for imaging at least one body part of the patient with the diagnostic imaging system, wherein the imaging procedure comprises taking a plurality of diagnostic images from different projection angles relative to the at least one body part, wherein the different projection angles comprise at least two of an anterior/posterior projection angle, a lateral projection angle, and various oblique angles;
   verify, with the body positioning system, that the at least one body part of the patient is positioned for imaging by the diagnostic imaging system; and
   obtain, using the imaging procedure, the plurality of diagnostic images of the at least one body part.

* * * * *